United States Patent [19]

Dessau et al.

[11] Patent Number: 4,922,050
[45] Date of Patent: May 1, 1990

[54] CATALYTIC DEHYDROGENATION OF HYDROCARBONS OVER INDIUM-CONTAINING CRYSTALLINE MICROPOROUS MATERIALS

[75] Inventors: Ralph M. Dessau, Edison; Randall D. Partridge, Trenton, both of N.J.; Ernest W. Valyocsik, Yardley, Pa.

[73] Assignee: Mobil Oil Corporation, New York, N.Y.

[21] Appl. No.: 353,584

[22] Filed: May 18, 1989

Related U.S. Application Data

[63] Continuation of Ser. No. 138,430, Dec. 28, 1987, Pat. No. 4,849,567.

[51] Int. Cl.$^5$ ............................................. C07C 5/333
[52] U.S. Cl. ...................... 585/379; 585/380; 585/444; 585/629; 585/660; 423/306; 423/326
[58] Field of Search ............... 585/660, 444, 379, 380, 585/629

[56] References Cited

U.S. PATENT DOCUMENTS

| | | | |
|---|---|---|---|
| Re. 29,948 | 3/1979 | Dwyer et al. | 208/110 |
| 3,702,293 | 11/1972 | Hayes et al. | 208/139 |
| 3,702,294 | 11/1972 | Rausch | 208/139 |
| 3,878,131 | 4/1987 | Hayes | 252/466 PT |
| 4,078,743 | 3/1978 | Kogan | 585/660 |
| 4,104,320 | 8/1978 | Bernard et al. | 260/673.5 |
| 4,175,031 | 11/1979 | Antos | 585/660 |
| 4,310,440 | 1/1982 | Wilson | 502/208 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,416,806 | 11/1983 | Bernard et al. | 502/74 |
| 4,418,006 | 11/1983 | Kim et al. | 502/73 |
| 4,435,283 | 3/1984 | Buss et al. | 208/138 |
| 4,435,311 | 3/1984 | Sikkenga | 585/660 |
| 4,440,871 | 4/1984 | Lok | 585/660 |
| 4,456,527 | 6/1984 | Buss et al. | 208/89 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Nordstrand | 502/66 |
| 4,551,574 | 11/1985 | Imai | 585/660 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/66 |
| 4,849,567 | 7/1989 | Dessau et al. | 585/379 |

FOREIGN PATENT DOCUMENTS

| | | |
|---|---|---|
| 74651 | 9/1981 | European Pat. Off. . |
| 0043562 | 1/1982 | European Pat. Off. . |
| 0107389 | 4/1984 | European Pat. Off. . |
| 0121232 | 10/1984 | European Pat. Off. . |
| 0121233 | 10/1984 | European Pat. Off. . |
| 0158348 | 10/1985 | European Pat. Off. . |
| 0158349 | 10/1985 | European Pat. Off. . |
| 0158350 | 10/1985 | European Pat. Off. . |
| 0158975 | 10/1985 | European Pat. Off. . |
| 0158976 | 10/1985 | European Pat. Off. . |
| 0158977 | 10/1985 | European Pat. Off. . |
| 0161488 | 11/1985 | European Pat. Off. . |
| 0161489 | 11/1985 | European Pat. Off. . |
| 0161490 | 11/1985 | European Pat. Off. . |
| 0161491 | 11/1985 | European Pat. Off. . |
| 3115324 | 11/1982 | Fed. Rep. of Germany . |
| 8202272 | 6/1982 | Netherlands . |
| 2033358 | 5/1980 | United Kingdom . |
| 2114150 | 8/1983 | United Kingdom . |

OTHER PUBLICATIONS

G. Wengui et al., "IR Study of Framework Vibrations and Surface Properties of High Silica Zeolites", Zeolites, Elsevir Science, Amsterdam, 1985, p. 279.
Huagong, vol. 15, No. 7 (1986) (with translation).
Ione, "Structure and Reactivity of Modified Zeolites", Elsevir Science, (1984), pp. 151-155.

*Primary Examiner*—Asok Pal
*Attorney, Agent, or Firm*—Alexander J. McKillop; Charles J. Speciale; Marina V. Schneller

[57] ABSTRACT

A catalytic dehydrogenation to produce the unsaturated analogs of aliphatic compounds with high process selectivity for the unsaturated analog production. The catalytic dehydrogenation comprises contacting the aliphatic compound, under dehydrogenation conditions, with a catalyst composition comprising a dehydrogenation metal and indium containing non-acidic crystalline microporous material.

5 Claims, 3 Drawing Sheets

4,922,050

CATALYTIC DEHYDROGENATION OF HYDROCARBONS OVER INDIUM-CONTAINING CRYSTALLINE MICROPOROUS MATERIALS

CROSS-REFERENCE TO RELATED APPLICATION

This is a continuation of Ser. No. 138,430, filed Dec. 28, 1987, now U.S. Pat. No. 4,859,567.

FIELD OF THE INVENTION

The invention relates to catalytic dehydrogenation of $C_2$–$C_5$ aliphatic paraffins. The catalytic dehydrogenation requires as the catalyst composition a non-acidic microporous crystalline material containing indium and dehydrogenating metal. The dehydrogenation proceeds with high selectivity for the olefin product.

BACKGROUND OF THE INVENTION

Dehydrogenation of $C_2$–$C_5$ aliphatic compounds produces known compounds, the corresponding unsaturated analog. The products can be employed in various processes. The most likely use of the products produced by the invention is in conversion processes to produce a variety of petrochemicals or liquid fuels like poly gasoline, motor alkylate and methyl tertiary butyl ether.

Dehydrogenation requirements of each of the members of the group $C_2$–$C_5$ alkanes differ. Those differing requirements reflect the reaction pathways involved and the thermodynamic properties of the starting materials and of the products. For example, butane dehydrogenation conditions can also effect butane isomerization and cracking, as major side reactions, which decrease the selectivity of the specific reaction for the product. When catalyzed by a solid catalyst, those cracking side-reactions can result in coking and/or aging of the catalyst necessitating regeneration procedures.

SUMMARY OF THE INVENTION

In accordance with the invention, dehydrogenation of an aliphatic of $C_2$–$C_5$ carbon atoms substituted or unsubstituted is catalyzed by a composition comprising a non-acidic, crystalline microporous material containing indium and dehydrogenation-hydrogenation metal. The dehydrogenation process of the invention does not catalyze isomerization or cracking either reactants or products with any significant degree of selectivity.

Dehydrogenation may be conducted in the presence or absence of purposefully added hydrogen and in the presence of diluents inert to conditions of the catalytic dehydrogenation such as nitrogen, helium and methane.

DETAILED DESCRIPTION OF THE INVENTION

Figure 1:
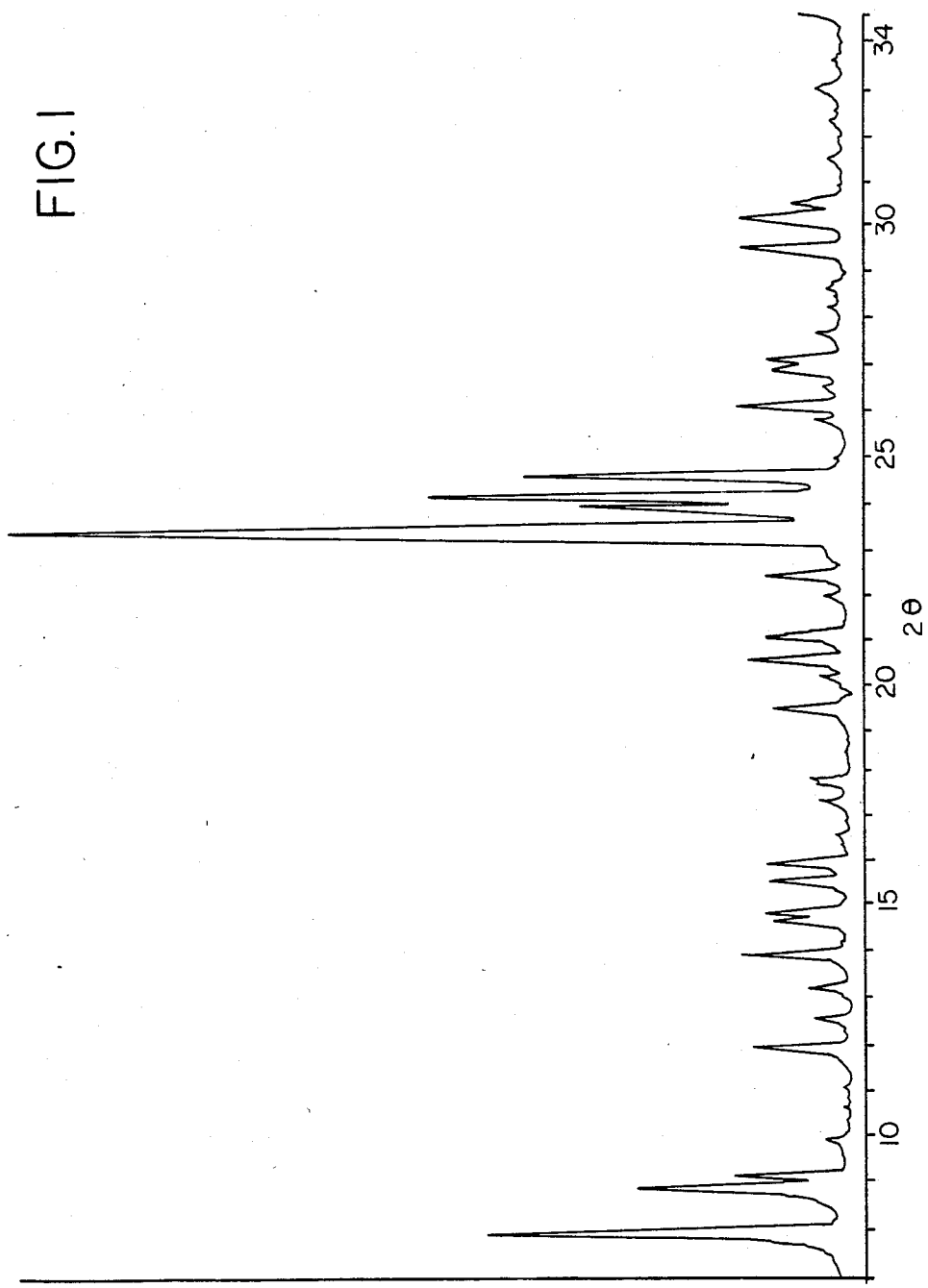

The process of the invention is a catalytic, dehydrogenation of an aliphatic to produce the corresponding unsaturated analog together with hydrogen ($H_2$). The catalytic dehydrogenation exhibits high selectivity with respect to production of said unsaturated analog, with substantially little, if any, selectivity for hydrogenolysis (cracking) and with substantially little, if any, selectivity for isomerization.

The feedstocks comprise at least one unsubstituted or substituted straight or branched chain aliphatic compound in which the aliphatic moiety has two to five carbon atoms. In accordance with the invention, dehydrogenation of the aliphatic moiety occurs to yield the unsaturated analog. When the aliphatic moiety is substituted, the substituents can be aryls substituted or unsubstituted. The class of reactants includes alkanes of 2 to 5 carbon atoms including ethane, propane, butane, isobutane, pentane and 2-methylbutane. Dehydrogenation of those respective alkane reactants will yield ethylene, propylene, butene, isobutene, pentene and isopentene, respectively.

The class of reactants includes olefins of 2 to 5 carbon atoms such as ethylene, butene, pentene, and isopentene. Dehydrogenation of ethylene will produce acetylene; dehydrogenation of butene will produce butadiene and dehydrogenation of methyl butene will produce isoprene.

The class of reactants employed in the dehydrogenation of the invention includes aryl substituted aliphatics, alkylaryl substituted aliphatics. Preferably, the alkyl group of the alkylaryl substituted aliphatic contains less than four carbon atoms and more preferably more than 1 carbon atom. The aryl substituted aliphatic reactants embrace unsubstituted arylaliphatics and alkyl substituted aryl aliphatics and; similarly, each of the alkyls of said alkyl substituted alkylaryls contains preferably less than 4 carbon atoms. By way of illustration reactants such as ethylbenzene, diethylbenzene, ethyl toluene, and cumene are representative of these compounds. On dehydrogenation in accordance with the invention, ethyl benzene will produce styrene; p-ethyltoluene will produce p-methylstyrene; cumene, isopropenylbenzene; and diethylbenzene, divinylbenzene.

In accordance with the invention, catalytic dehydrogenation conditions include pressures varying from subatmospheric, to atmospheric to greater than atmospheric. Preferred pressures range from 0.1 atmospheres to atmospheric. However, pressures up to 500 psig can be employed. The dehydrogenation is conducted at elevated temperatures ranging from 300° C. to 700° C.; preferably, the temperatures range from 300° C. to 600° C. and most preferably from 400° C. to 600° C. Reactor inlet $H_2$/feed ratios are 5 or less; even at reactor inlet ratios of zero (0), there will be a hydrogen partial pressure in the reactor because hydrogen is a bi-product of dehydrogenation. The liquid hourly space velocity is 0.1 to 50, preferably 0.5 to 10.

Under these conditions, the catalytic dehydrogenation of the invention exhibits little if any selectivity for hydrogenolysis or for isomerization. Accordingly, the process of the invention exhibits low, if any, selectivity for hydrogenolysis (with products of fewer carbon atoms than the reactants) and low selectivity for isomerization.

BRIEF DESCRIPTIONS OF DRAWINGS

Figure 2:
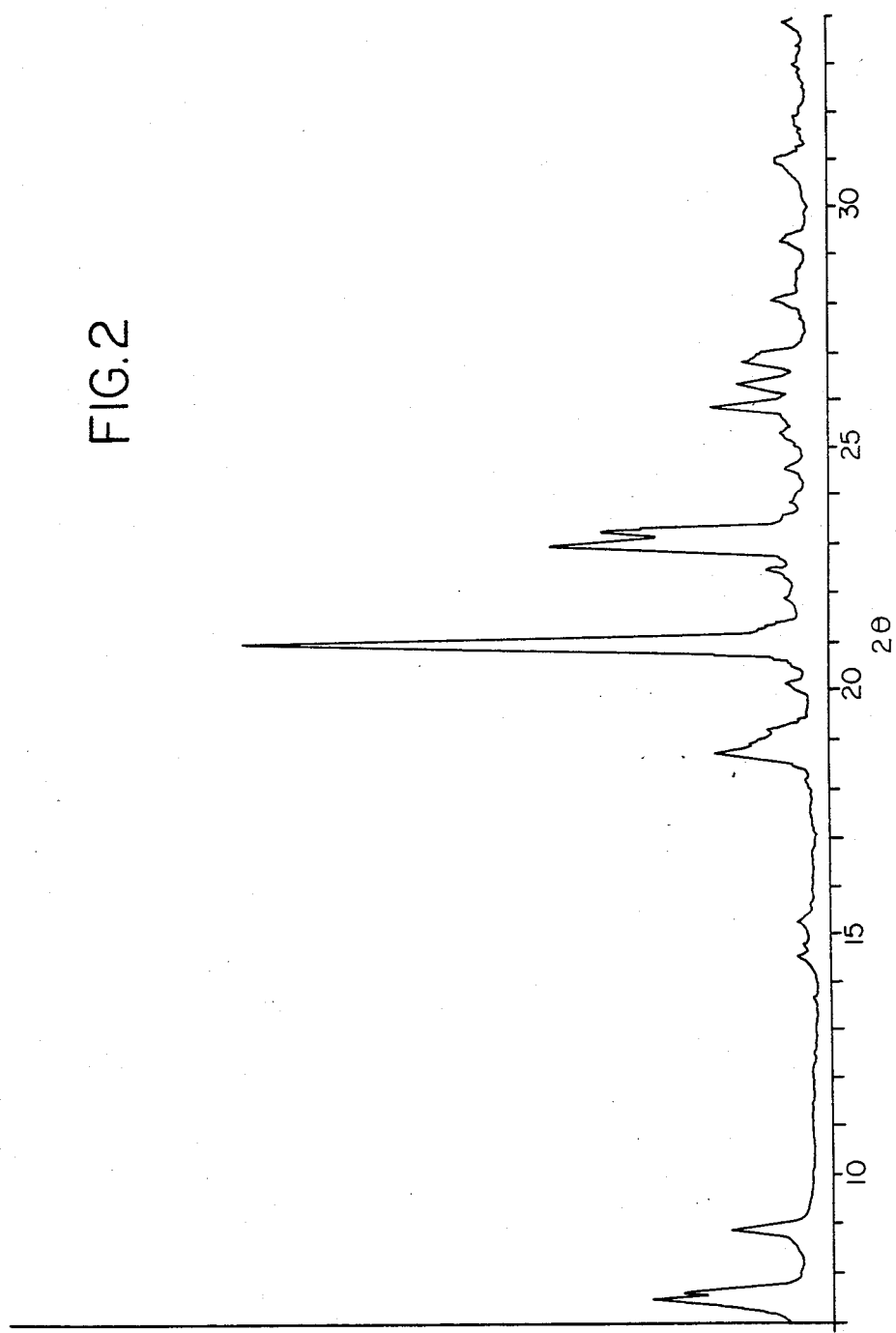
Figure 3:
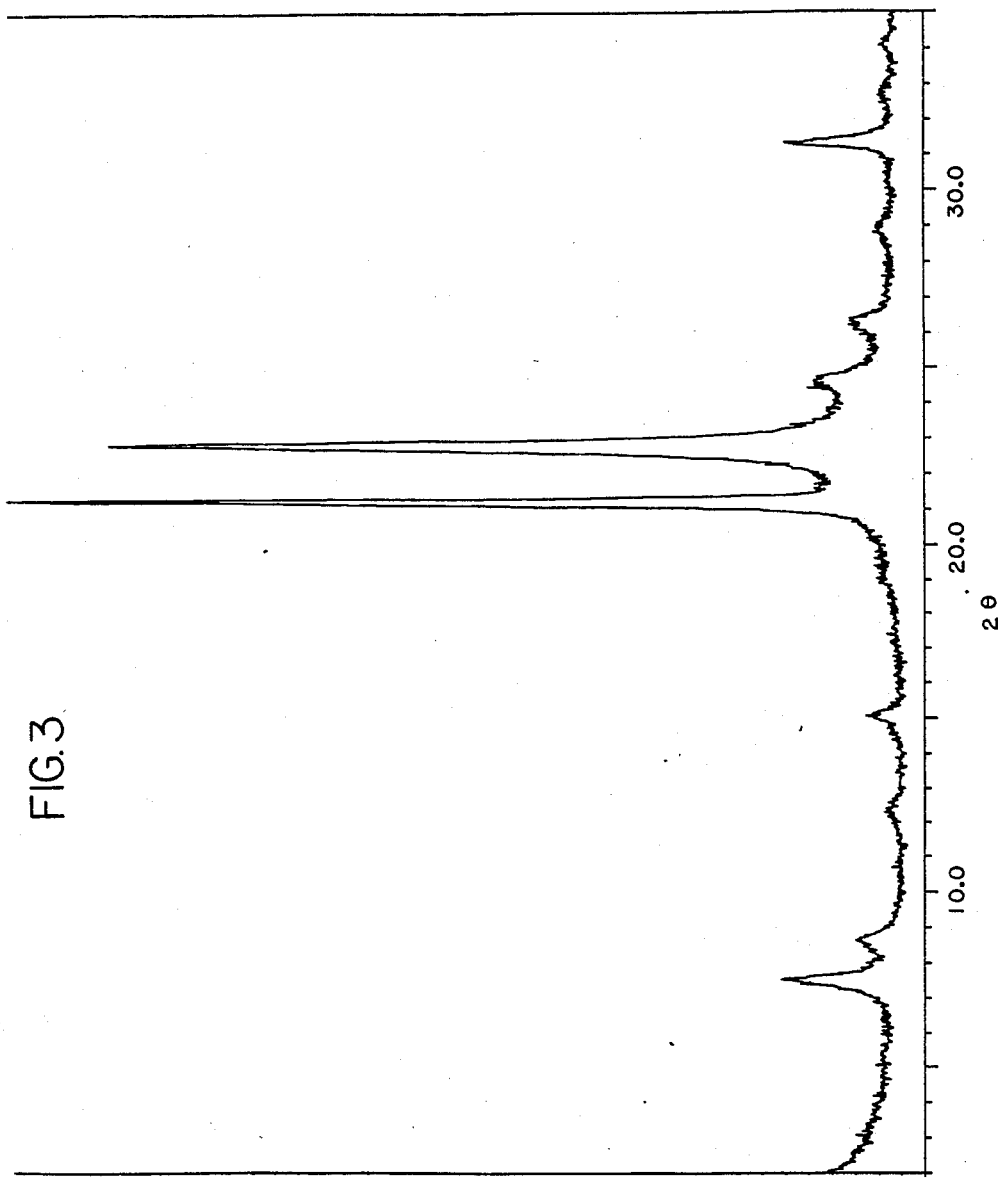

FIGS. 1-3 are the x-ray diffraction patterns of various In-ZSM zeolites.

The catalyst for the catalytic dehydrogenation of the invention comprises a hydrogenation/dehydrogenation metal and an indium containing non-acidic, crystalline microporous material. The hydrogenation/dehydrogenation metal can be any Group VIII metal, such as nickel, or chromium or vanadium; preferably it is from the platinum group metals; and most preferably it is platinum.

The amount of hydrogenation/dehydrogenation metal in the catalyst can range from 0.01 to 30 weight percent and preferably from 0.02 to 10 weight percent of the crystalline indium containing materials.

The indium content of the crystalline materials can range from 0.01 to 20 weight percent. Practically, the indium content will range from 0.1 to 10 weight percent.

Preferred crystalline indium containing materials of the invention are zeolites characterized by Si/Al ratios of at least 2. However, the silica:alumina ratio of the zeolite can be up to 1000, or greater. In specific embodiments the aluminum content of some of these materials is less than 0.1 weight percent.

The crystalline indium containing material of the invention can contain other elements including boron, iron, chromium and gallium. The content of these other elements in the crystalline indium containing materials can range from 0 to 10 weight percent.

The indium containing precursors of the invention, described herein, are crystalline in the sense that they are identifiable as isostructural with zeolites by X-ray powder diffraction pattern. The crystalline microporous indium containing material has an X-ray diffraction pattern which corresponds to a zeolite, SAPO, ALPO, etc. For example, indium compositions of the invention have been made the crystal structure of which is that of ZSM-5, ZSM-11, ZSM-12 ZSM-23, ZSM-48, ZSM-50, zeolite Beta, ZSM-20, SAPO-5 and ALPO-5. These are characterized by pore sizes up to about 8 Angstroms. The X-ray diffraction pattern and significant lines Tables of these materials have been described in the U.S. Patent literature. In a preferred embodiment the pore size of the microporous crystalline indium containing materials ranges from about 5 to about 8 Angstroms.

The term "microporous" as it refers to such material relates to pores, or channels, with diameters of less than 20 Angstroms. Examples of these microporous crystalline materials include crystalline silicates, crystalline alumino-silicates (zeolites), crystalline ALPOs, crystalline SAPO and related compositions and intercalated pillared materials derived from clays, layered silicates and titanates. The crystalline silicate, alumino silicate (zeolites), ALPOs and SAPOs, have pores of uniform size and channel systems which are uniquely determined by unit structure of the material. The uniform pore size and/or channel systems allow such a material to selectively absorb molecules of certain dimensions and shapes. In the art, microporous material having pores, or channels, of less than 20 Angstroms, can be divided into small, medium and large pore by the diameters of those pores, or channels. The pores of the small pore material have an average diameter of less than 5 Angstroms; medium size pores range from an average diameter of about 5 to about 7 Angstroms, and large pore silicates indicates a diameter of greater than about 7. The word "average" is used to refer to diameter to embrace those species in which the pore is elliptical. Alternatively, the demarcation between small, medium and large pore materials can be based on the following sorption properties (measured at room temperature for crystallites having a minimum dimenson of 0.1 micron):

1. Small pore: $n-C_6/i-C_6$ sorption ratio greater than approximately 10.

2. Medium pore: $n-C_6/i-C_6$ is less than 10 and $n-C_6$/Mesitylene sorption ratio greater than approximately 5.

3. Large pore: $n-C_6$/Mesitylene sorption ratio less than approximately 5.

In the art, zeolites are a subclass of crystalline microporous silicates. Zeolites can contain aluminum as well as silicon. In some zeolites, the upper limit of the silicon/aluminum atomic ratio is unbounded. ZSM-5 is one such example wherein the silicon/aluminum atomic ratio is at least 2.5 and up to infinity. By way of illustration, U.S. Pat. No. 3,941,871, reissued as No. Re. 29,948, discloses a porous crystalline silicate made from a reaction mixture containing no deliberately added aluminum and exhibiting the X-ray diffraction pattern characteristic of ZSM-5 zeolites.

Zeolites can be acidic or non-acidic, depending on the framework aluminum content and on the amount of compensating cations, such as $Na^+$, $K^+$, etc. ALPOs described in U.S. Pat. No. 4,310,440, which is incorporated by reference herein, are neutral. SAPOs described for example in U.S. Pat. No. 4,440,871, which is incorporated by reference herein, can be acidic or non-acidic depending on the ratio of framework Al:P therein and the compensating cation, such as $Na^+$, $K^+$ (other than proton species and other than proton forming species such as $NH_4^+$). ELAPOs are described in U.S. Pat. No. 4,500,651, while MeAPOs are described in U.S. Pat. Nos. 4,544,143 and 4,567,029, each of said latter three patents being incorporated by reference herein.

The compositions comprising hydrogenation/dehydrogenation metal combined with the crystalline indium containing materials do not exhibit any appreciable acid activity. These catalysts would meet the criteria of non-acidic catalysts described by Davis and Venuto, J. CATAL. Vol. 15, p.363 (1969). Thus, a non-equilibrium mixture of xylenes are formed from either n-octane or each individual methylheptane isomer, with the octane yielding more o-xylene and 2-methyl-heptane yielding mostly m-xylene, at conversions between and 10 and 60%. Alternatively, the non-acidic compositions will exhibit a pH of at least 6 when added to distilled deionized pH7 water maintained under inert (such as argon) atmosphere; by an inert atmosphere in this context it means an atmosphere free of $CO_2$. Typically, in these tests, 100 mg of catalyst was added to 30 ml. of distilled deionized water. Some compositions will exhibit a pH of at least 7.5.

When, as in embodiments herein, the crystalline indium dehydrogenation metal containing material exhibits an X-ray diffraction pattern of a zeolite, at least some of the dehydrogenation metal may be intrazeolitic, that is, some of that metal is within the pore structure of the crystal, although some of that metal can be on the surface of the crystal. A test for determining whether, for example, platinum is intrazeolitic or extrazeolitic in the case of ZSM-5 is reported by R. M. Dessau, J. CATAL. Vol. 89, p. 520 (1984). The test is based on the selective hydrogenation of olefins.

Compositions of the invention used in catalysis decrease the hydrogen content of the reactant to produce a product having the same number of carbon atoms as the number of carbon atoms in the reactant. By comparison indium-free counterparts of those compositions catalyzed also hydrogenolysis of paraffins, e.g., to methane, as a major competing side reaction; and, accordingly, the latter compositions exhibit decreased selectivity for the aromatization of paraffins but increased selectivity for $C_1-C_5$ paraffin production. Some of the aforementioned catalysts were screened for hexane and heptane aromatization at 538° C. in the presence of nitrogen diluent. The results are shown in Table A below in which the crystalline silicate employed exhibited the diffraction pattern of a ZSM-5.

TABLE A

Paraffin Aromatization over Pt/Containing Non-acidic Silicates Isostructural with ZSM-5

| Support | Paraffin | Conversion | Benz. Sel.[c] | Tol. Sel. | C5-Sel |
|---|---|---|---|---|---|
| B/ZSM-5 | n-hexane | 52% | 31% | — | 12%[a] |
| " | " | 98% | 51% | 2% | 40%[a] |
| " | heptane | 56% | 56% | 8% | 7%[a] |
| " | " | 95% | 33% | 31% | 34%[a] |
| In/ZSM-5 | n-hexane | 60% | 81% | — | 1% |
| " | " | 99+% | 95% | — | 4% |
| " | heptane | 50% | — | 92% | 1% |
| " | " | 99% | — | 97% | 1% |
| Si/ZSM-5[b] | n-hexane | 58% | 69% | — | 18%[a] |
| " | " | 99% | 72% | — | 26%[a] |
| " | heptane | 34% | 45% | 17% | 14%[a] |
| " | " | 99% | 62% | 4% | 34%[a] |

[a] primarily methane.
[b] high silica/alumina ZSM-5.
[c] $H_2$-free selectivity based on carbon The non-acidic platinum catalyst prepared from In/ZSM-5 provided much higher aromatics selectivity than all the other catalysts examined. Benzene yields from hexane were as high as 95%, while heptane produced toluene in 97% yield ($H_2$ free carbon base).

The other catalysts, including Pt/B-ZSM-5 and Pt/high silica:alumina ratio enumerated in the Table did not show any appreciable acid activity, in that platinum chemistry dominated. Significant metal-catalyzed aromatization was observed; however hydrogenolysis to methane constituted a major competing side reaction. The highest toluene selectivity observed was 50–55%, and in most cases that selectivity was significantly lower. This is in sharp contrast to the aromatic product selectivity of the platinum/In/ZSM-5. The cause for this difference in platinum behavior from the Pt/In-ZSM-5 catalyst is not clear.

SYNTHESIS OF THE COMPOSITIONS

The crystalline indium-materials can be made in various ways. Indium incorporation can be during synthesis or post-synthesis; and the materials can be prepared either by stepwise or simultaneous incorporation of the indium and the hydrogenation/dehydrogenation function. The dehydrogenation function can be first introduced to the synthesis product with subsequent indium incorporation, or vice versa. Stepwise preparation includes techniques of cocrystallization, impregnation, or exchange. Crystallization can be undertaken in a two phase system described in commonly assigned Ser. No. 878,555, filed June 26, 1986. Other elements such as boron, iron chromium, gallium, can also be included. Simultaneous incorporation includes the combination of indium with the dehydrogenation/hydrogenation function during synthesis (i.e., crystallization) or simultaneously after synthesis of the crystalline material.

An indium free material can be treated with indium compounds at elevated temperatures. Such treatments can be conducted so that the source of indium is either in the gaseous (such as indium chloride) or the liquid phase including the aqueous phase (such as indium nitrate). Alternatively, an indium free crystalline reactant can simply be impregnated with indium source and then calcined at temperatures above 400° C.

The indium free reactant may have high silica:alumina ratios or contain other elements such as boron, chromium, iron, and gallium. Reactants and products containing 0.1 weight percent or less aluminum are the preferred embodiments of the examples. In materials of the invention, all cation-exchangeable sites are occupied by non-hydrogen (non-proton) and by non-hydrogen precursors, such as $NH_4^+$. Specifically, such sites are occupied by $Na^+$, $K^+$, $Cs^+$ or admixtures thereof. The alkali metals serve to neutralize any acidity due to framework aluminum. The source of alkali metal cation can derive from cations incorporated during synthesis, in excess of the aluminum content thereof. Alternatively, one can treat the final product with a basic solution of an alkali metal hydroxide as a final step prior to use, as described for example in U.S. Pat. No. 4,652,360.

The non-acidic, crystalline, microporous, indium modifier and dehydrogenation metal containing materials of the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. When used in dehydrogenation and/or dehydrocyclization, the material of the invention will preferably be combined with non-acidic matrix or binder materials. A preferred matrix or binder material would be silica.

These compositions of the invention exhibit high selectivity for dehydrogenation and/or dehydrocyclization, which is evidenced by the following examples.

EXAMPLES

Example A

A 0.5% platinum/indium-ZSM-5 catalyst was prepared from the silica-bound synthesized indium ZSM-5 of Run No. 8 in Table 1A below. Platinum in-corporation into the sample followed calcination of the sample; the calcined sample was stirred in an aqueous solution of $Pt(NH_3)_4Cl_2$ at room temperature overnight. It was then washed, filtered and dried and then calcined in oxygen in a temperature programmed calcination to maximum temperature of about 350° C.

The "non-acidic" nature of the catalyst was confirmed by its ability to aromatize n-heptane to toluene in high yield. At 500° C. and 30 torr heptane in nitrogen, toluene was formed in greater than 90% selectivity. Furthermore, the small amounts of both methane and propane produced were exceeded by the ethane formed, indicative of the low hydrogenolysis and acid activity of the catalyst.

Propane dehydrogenation was studied at 538° C. and 1 atmosphere. At conversion levels approaching equilibrium (27%) propylene was formed in better than 98% selectivity (i.e. $C_1+C_2$ represented less than 2% of the products formed.)

Example B

Under similar conditions, n-butane yielded 28.6% butenes at 30.1% conversion (a selectivity of 95%). Iso-butane gave 30.2% isobutene at 30.9% conversion (a selectivity of 97.5%). These and other results are summarized in the Table below:

| Paraffin | % Conversion | Selectivity to Olefins |
|---|---|---|
| Propane | 26.5 | 98.5% |
| " | 18.0 | 99.0% |
| n-Butane | 36.6 | 93.0% |
| " | 30.1 | 95.0% |

-continued

| Paraffin | % Conversion | Selectivity to Olefins |
|---|---|---|
| " | 21.9 | 97.0% |
| iso-Butane | 45.3 | 94.6% |
| " | 38.0 | 96.9% |
| " | 30.9 | 97.5% |

Example C

Indium-containing compositions which can be used in the process of the invention are described in Examples C-L below.

Crystalline silicate products were produced containing indium and exhibiting characteristic X-ray diffraction patterns of structures corresponding to ZSM-5, ZSM-11, ZSM-12, ZSM-23, ZSM-48 and ZSM-50.

Table 1A compiles the composition ranges employed in the synthesis of a series of In/ZSM-5 products with widely varying indium content. Also shown in Table 1A is the synthesis of indium-containing silicates having X-ray pattern of ZSM-11, ZSM-12, ZSM-23, ZSM-48 and ZSM-50. The footnotes in Table 1A specify the $SiO_2$ sources and the organic directing agents employed in the synthesis.

TABLE 1A

Crystallizations of Indium-Containing Zeolites
160° C.; Stirred 400 rpm

| | Mixture Composition (Mole Ratios) | | | | | | |
|---|---|---|---|---|---|---|---|
| Run # | $\frac{SiO_2}{In_2O_3}$ | $\frac{H_2O}{SiO_2}$ | $\frac{OH-}{SiO_2}$ | $\frac{NA+}{SiO_2}$ | $\frac{R}{SiO_2}$ | Time, Days | Zeolite Product |
| 1[a] | 500 | 48 | 0.26 | 0.27 | 0.10[c] | 3 | ZSM-5 |
| 2[b] | 500 | 48 | 0.26 | 0.27 | 0.10[c] | 3 | ZSM-5 |
| 3[a] | 300 | 48 | 0.26 | 0.28 | 0.10[c] | 3 | ZSM-5 |
| 4[b] | 300 | 48 | 0.26 | 0.28 | 0.10[c] | 1 | ZSM-5 |
| 5[d] | 300 | 48 | 0.26 | 0.28 | 0.20[b] | 1 | ZSM-5 |
| 6[b] | 200 | 48 | 0.26 | 0.30 | 0.10[e] | 4 | ZSM-48 |
| 7[b] | 200 | 48 | 0.26 | 0.30 | 0.10[f] | 4 | ZSM-11 |
| 8[b] | 150 | 48 | 0.26 | 0.31 | 0.10[c] | 2 | ZSM-5 |
| 9[b] | 150 | 48 | 0.26 | 0.31 | 0.10[c] | 2 | ZSM-5 |
| 10[b] | 150 | 48 | 0.26 | 0.31 | 0.10[c] | 2 | ZSM-5 |
| 11[b] | 150 | 48 | 0.26 | 0.31 | 0.10[c] | 3 | ZSM-5 |
| 12[b] | 150 | 48 | 0.26 | 0.31 | 0.10[c] | 2 | ZSM-5 |
| 13[b] | 100 | 48 | 0.26 | 0.34 | 0.08[g] | 3 | ZSM-12 |
| 14[h] | 76 | 48 | 0.26 | 0.59 | 0.10[c] | 6 | ZSM-5 |
| 15[i] | 70 | 40 | 0.20 | 0.23 | 0.10[c] | 3 | ZSM-5 |
| 16[b] | 70 | 40 | 0.26 | 0.37 | 0.10[c] | 3 | ZSM-5 |
| 17[a] | 60 | 48 | 0.26 | 0.39 | 0.10[c] | 3 | ZSM-5 |
| 18[b] | 150 | 40 | 0.20 | 0.25 | 0.10[j] | 3 | ZSM-23 |
| 19[b] | 300 | 40 | 0.20 | 0.23 | 0.10[j] | 3 | ZSM-23 |
| 20[b] | 300 | 40 | 0.20 | 0.23 | 0.10[k] | 3 | ZSM-50 |

[a]Silica source is tetraethylorthosilicate ($Et_4SiO_4$)
[b]Silica source is SPEX Industries precipitated $SiO_2$
[c]R = TPA+
[d]Silica source is DeGussa fumed $SiO_2$
[e]R = DIQUAT-6 = $(CH_3)_3N(CH_2)_6N(CH_3)_3$
[f]R = TBA+
[g]R = $(CH_3)_3N(CH_2)_3N(CH_3)_2$
[h]Q-brand sodium silicate
[i]Silica source is kieselsaure precipitated $SiO_2$
[j]R = DIQUAT-7 = $(CH_3)_3N(CH_2)_7N(CH_3)_3$
[k]R = Dibenzyldimethylammonium ion Table 2A is a compilation of chemical analyses of some of our indium-containing products. These products vary in indium content from 0.36–5.20 wt % In. The formulas of the zeolite products are expressed in Table 2 as a ratio of oxides per mole of $In_2O_3$.

Example D

The In/ZSM-5 of that run No. 12 was prepared as follows:

The source of the indium can be incorporated into the zeolitic silicate synthesis reaction mixture as a partial, or preferably as a complete substitute for sources of alumina (or boron) conventially used in zeolite synthesis. In the embodiments described below the crystalline indium containing silicates were synthesized from crystallization reaction mixtures which contained no deliberately added sources of $Al_2O_3$.

A commercial silica gel (SPEX Ind.) with very low aluminum contamination was employed in the synthesis of In-ZSM-5. First, 0.85 g $In(NO_3)_3$ and 2.66 g NaOH pellets were dissolved in 180.2 g de-ionized water, then 5.64 g tetrapropylammonium bromide (TPABr) was dissolved in this basic solution. This solution was transferred to a 300 ml stainless steel autoclave, and 15.0 g of silica gel (SPEX) was added. The autoclave was then sealed and stirring and heating was begun. The hydrogel formed by this reaction mixture is described by the following mole ratios:

| $SiO_2/In_2O_3$ | : | $H_2O/SiO_2$ | : | $OH-/SiO_2$ | : | $Na+/SiO_2$ | : | $TPA+/SiO_2$ |
|---|---|---|---|---|---|---|---|---|
| 150 | : | 48 | : | 0.26 | : | 0.31 | : | 0.10 |

The hydrogel was reacted at 160° C. for 2 days at a stirring rate of 400 rpm before quenching. The resultant crystalline product was filtered, washed, and dried.

X-ray powder diffraction analysis showed the product to be 100% crystalline ZSM-5, when compared to the diffraction pattern of a conventional ZSM-5. Elemental analysis of the ZSM-5 product gave: C=7.93 wgt %, N=0.74%, Na=0.56%, In=2.26%, Al 0.005%, SiO$_2$=83.85%, Ash=88.05%.

TABLE 2A

Analyses of Some Indium-Containing Zeolitic Silicate Products

| Sample Run from No. | Weight Percent | | | | | | | Moles C Moles N | Moles per Mole In$_2$O$_3$ | | | |
|---|---|---|---|---|---|---|---|---|---|---|---|---|
| | C | N | Na | In | SiO$_2$ | Al$_2$O$_3$ | Ash | | N$_2$O | Na$_2$O | Al$_2$O$_3$ | SiO$_2$ |
| 15 | 6.96 | 0.66 | 3.28 | 5.20 | 62.47 | 0.070 | 85.34 | 12.3 | 1.04 | 3.15 | 0.03 | 46 |
| 14 | 6.74 | 0.43 | 2.64 | 4.19 | 69.94 | 0.24 | 86.20 | 18.3 | 0.84 | 3.14 | 0.13 | 64 |
| 16 | 7.02 | 0.56 | 0.79 | 3.48 | 76.45 | 0.035 | 84.78 | 14.6 | 1.32 | 1.13 | 0.02 | 84 |
| 13 | 6.01 | 0.61 | 0.65 | 2.79 | 81.83 | 0.031 | 91.79 | 11.2 | 1.79 | 1.16 | 0.025 | 112 |
| 9 | 8.02 | 0.71 | 0.98 | 2.11 | 74.85 | 0.078 | 88.05 | 13.6 | 2.36 | 2.29 | 0.06 | 132 |
| 8 | 8.01 | 0.68 | 1.48 | 2.14 | 74.64 | 0.11 | 88.72 | 13.7 | 2.61 | 3.45 | 0.11 | 133 |
| 12 | 7.93 | 0.74 | 0.56 | 2.26 | 83.85 | 0.005 | 88.05 | 12.4 | 2.68 | 1.23 | 0.009 | 142 |
| 10 | 8.37 | 0.81 | 1.83 | 1.92 | 73.14 | 0.025 | 88.36 | 12.0 | 3.46 | 4.76 | 0.03 | 146 |
| 11 | 8.22 | 0.62 | 0.54 | 1.49 | 82.14 | 0.031 | 85.96 | 15.5 | 3.41 | 1.81 | 0.05 | 211 |
| 6 | 4.58 | 0.79 | 0.48 | 1.46 | 86.70 | 0.029 | 91.86 | 6.7 | 4.44 | 1.64 | 0.045 | 227 |
| 7 | 8.66 | 0.51 | 0.44 | 0.96 | 82.29 | 0.013 | 89.43 | 19.8 | 4.36 | 2.29 | 0.045 | 328 |
| 2 | 8.12 | 0.69 | 0.40 | 0.36 | 78.05 | 0.083 | 85.69 | 13.7 | 15.7 | 5.55 | 0.52 | 830 |

These results expressed in mole ratios were: C/N=12.5; Moles/mole In$_2$O$_3$: N$_2$O=2.68, Na$_2$O=1.23, Al$_2$O$_3$=0.009, SiO$_2$=142.

Platinum incorporation was undertaken as follows: The as-synthesized zeolite was heated in nitrogen to 520° C. at 1° C./min and held there for 6 hours. It was then calcined in air in a similar manner. The calcined zeolite analyzed for 41.05% Si, 2.21% In (Si/In2=152), and 120 ppm Al, and sorbed 10.4% n-hexane at 90° C. The calcined zeolite (3 g) was stirred in a solution of 150 mg Pt(NH$_3$)$_4$Cl$_2$ in 100 ml water at room temperature overnight. After being washed, filtered and dried, the ion-exchanged zeolite was found to contain 0.41 meq NH$_3$/g ash, which is equivalent to 1.89% Pt on sample. The platinum tetramine zeolite was then calcined in oxygen to 350 C. at 0.5 C./min and held there for 1 hour. Elemental analysis indicated the presence of 1.85% Pt on the final catalyst.

At very high hexane conversions (99%), benzene was formed in over 94% yield. Similarly, n-heptane yielded 96% toluene. Similarly, n-heptane yielded 96% toluene. Consistent with the non-acidic nature of this platinum catalyst, n-octane yielded predominantly ethylbenzene and ortho-xylene, 2-methylheptane produced mostly meta-xylene, and 3-methylheptane formed mainly ethylbenzene, para-, and ortho-xylene.

Example E

In Example C, zeolitic silicate was made using In(NO$_3$)$_3$ in the crystallization reaction mixture. Here, indium was incorporated post-synthesis; in a subsequent step platinum was ion-exchanged onto the zeolite.

In this example, a high silica/alumina (10,000) ZSM-11 was calcined in nitrogen and then in air at 538° C. InCl$_3$ vapors were passed through the zeolite in a stream of nitrogen, while it was heated to 500° C. at 10 C./min. The zeolite was maintained at 500° C. for 1.5 hours. After cooling, the catalyst was added to 200 ml 1M NH$_4$Cl adjusted to pH 9.5 with NH$_4$OH. The mixture was stirred for 20 minutes at room temperature, and then filtered. The zeolite was then reexchanged for 3 hours with 1M NH$_4$Cl adjusted to pH 7.6. Thermogravimetric analysis indicated the presence of 0.325 meq/g ammonium ion in the zeolite.

Platinum was incorporated by ion exchange with Pt(NH$_3$)$_4$Cl$_2$ at room temperature. The platinum zeolite was then calcined in oxygen to 350 C. at 0.5 C./min.

The "non-acidic" nature of the catalyst was confirmed by its ability to aromatize n-heptane to toluene in high yield. At about 500° C. (up to about 538° C.) and 30 torr heptane in nitrogen, toluene was formed in 94% selectivity at a conversion level of greater than 90%.

Example F

The ZSM-5-type borosilicate was synthesized at 170° C. from a mixture of 12.4 g high purity silica (SPEX), 105 g 20% TEA hydroxide, and 0.8 g boric acid. The as-synthesized zeolite was then calcined in nitrogen and then in air at 520° C. The calcined zeolite contained 41.39% Si, 0.015% Al, and 0.44% B.

Two grams of the calcined borosilicate was impregnated with 135 mg In(NO$_3$)$_3$, and calcined in air at 500° C. for 2 hours. 1.8 g of this material was then ion-exchanged with 28 mg Pt(NH$_3$)$_4$Cl$_2$ in 100 ml water at room temperature. TGA analysis in hydrogen indicated the presence of 0.18 meq N/g equivalent to 0.87% Pt. The platinum-exchanged zeolite was then calcined in oxygen to 350° C. at 0.5° C./min.

The catalyst activity of the foregoing composition was examined. The "non-acidic" nature of the catalyst was confirmed by its ability to aromatize n-heptane to toluene in high yield. At 500° C. and 30 torr heptane in nitrogen, toluene was formed in 95% yield. Furthermore, the small amounts of both methane and propane produced were exceeded by the ethane formed, indicative of the low hydrogenolysis and acid activity of the catalyst.

| % Conversion | % C1 | % C2 | % Benzene | % Toluene (Selectivity) |
|---|---|---|---|---|
| 96 | 0.4 | 0.6 | 1.3 | 92 (96%) |
| 99 | 0.5 | 1.0 | 1.5 | 95 (96%) |

Example G

Indium-containing zeolite ZSM-20 was synthesized by the following procedure:

12.75 grams of sodium aluminate (NaAlO$_2$) and 6.02 grams indium nitrate were dissolved in 57.96 grams of deionized water. After the solid ingredients dissolved, 484.1 ml of 2.88 N tetraethylammonium hydroxide (TEAOH) was added to the solution. The resulting solution was not stirred into 312.5 grams of tetraethylorthosilicate. This solution was kept stirring for one hour until the hydrolysis reaction was complete. The resulting hydrogel was now transferred to a one-liter polypropylene bottle.

The polypropylene bottle was loosely capped and placed into a steambox (100° C.) to promote the crystallization of the zeolite. The next morning the bottle was removed from the steambox and the bottle cap was now closed tightly. The bottle was shaken vigorously, then replaced into the steambox. The reaction mixture for the initial hydrogel formed for the synthesis of the indium-containing ZSM-20 can be described by the following set of mole ratios:

| | |
|---|---|
| $SiO_2/In_2O_3$ | 150 |
| $H_2O/SiO_2$ | 10 |
| $OH^-/SiO_2$ | 0.9 |
| $Na^+/SiO_2$ | 0.09 |
| $TEA^+/SiO_2$ | 0.93 |
| $SiO_2/Al_2O_3$ | 30 |

Samples of the solid product were removed daily from the polypropylene bottle for X-ray diffraction (XRD) analysis to determine the product crystallinity. XRD analysis showed that the ZSM-20 crystallization was complete in 14 days. The polypropylene bottle was removed from the steambox, and the solid product was filtered on a Büchner funnel. After filtration, the product zeolite was boiled in de-ionized water and again filtered and dried under an infrared heat lamp. After drying, a sample of the product was submitted for XRD and chemical analysis. XRD analysis showed the product to be zeolite ZSM-20. The chemical analysis for the indium-containing ZSM-20 was:

| Weight Percent | | | | | | |
|---|---|---|---|---|---|---|
| C | N | Na | In | $SiO_2$ | $Al_2O_3$ | Ash |
| 10.0 | 1.2 | 3.0 | 3.08 | 58.5 | 11.4 | 75.1 | which gives:

| Moles C | | Moles per Mole $In_2O_3$ | | | | | | |
|---|---|---|---|---|---|---|---|---|
| Moles N | $N_2O$ | : | $Na_2O$ | : | $Al_2O_3$ | : | $SiO_2$ |
| 9.7 | 3.19 | : | 4.86 | : | 8.33 | : | 72.7 |

Example H

Indium-containing zeolite Beta was synthesized in the following manner:

5.95 grams of sodium aluminate and 4.68 grams of indium nitrate were dissolved in 85.14 grams of de-ionized water. After the salts dissolved, 105.0 ml of 3.1N TEAOH was added to the solution. The resulting solution was transferred to a 300 ml stainless-steel autoclave.

Now 46.67 grams of solid silica gel (SPEX Industries) was pored into the autoclave, the autoclave was sealed and stirring and heating begun immediately. The reaction was carried out at 160° C. with stirring (400 rpm).

The initial reaction mixture for the synthesis of indium-containing zeolite Beta can be described by the mole ratios:

| | |
|---|---|
| $SiO_2/In_2O_3$ | 90 |
| $H_2O/SiO_2$ | 12 |
| $OH^-/SiO_2$ | 0.40 |
| $Na^+/SiO_2$ | 0.09 |
| $TEA^+/SiO_2$ | 0.46 |
| $SiO_2/Al_2O_3$ | 30 |

After 4 days the autoclave was quenched in a water plus ice bath to terminate the reaction. The solid product was filtered, boiled in water and again filtered. XRD analysis showed the crystalline product to be zeolite Beta. Chemical analysis of the indium-containing zeolite Beta product gave the following results:

| Weight Percent | | | | | | |
|---|---|---|---|---|---|---|
| C | N | Na | In | $SiO_2$ | $Al_2O_3$ | Ash |
| 10.84 | 1.71 | 1.4 | 2.5 | 69.8 | 4.2 | 79.92 | which gives:

| Moles C | | Moles per Mole $In_2O_3$ | | | | | |
|---|---|---|---|---|---|---|---|
| Moles N | $N_2O$ | : | $Na_2O$ | : | $Al_2O_3$ | : | $SiO_2$ |
| 7.4 | 5.61 | : | 2.79 | : | 3.78 | : | 62.8 |

Example I

Indium-containing crystalline aluminophosphate molecular sieve ALPO-5 was synthesized as follows:

23.1 grams of concentrated phosphoric acid (86.3% $H_3PO_4$) was diluted with 30.0 grams of de-ionized water. Now 10.0 grams of Kaiser alumina was stirred into this acid solution and the mixture was digested for 45 minutes at 90% C. with continuous stirring. After the digestion period a solution containing 1.18 grams of indium nitrate dissolved in 41.0 grams of de-ionized water was stirred into the gel. Finally, 37.0 grams of 40% wt. TEAOH solution was stirred into the gel and stirring continued until a uniform gel was produced. This gel was not transferred to a 300 ml stainless-steel autoclave. The resulting reaction mixture hydrogel can be described by the following mole ratios:

| | |
|---|---|
| $P_2O_5/Al_2O_3$ | 1.0 |
| $H_2O/Al_2O_3$ | 59 |
| $H^+/Al_2O_3$ | 7.2 |
| $In_2O_3/Al_2O_3$ | 0.02 |
| $TEA^+/Al_2O_3$ | 1.0 |

The autoclave was sealed and heated and stirring began immediately. The reaction was carried out at 160° C. with stirring (400 rpm).

After 4 days the autoclave was quenched in a water-+ice bath to terminate the crystallization. The solid product was filtered, boiled in water and filtered again. After drying the product, XRD analysis showed the material to be crystalline aluminophosphate designated by Union Carbide as ALPO-5. Chemical analysis of the indium-containing ALPO-5 gave:

| Weight Percent | | | | | | |
|---|---|---|---|---|---|---|
| C | N | Na | P | Al | In | Ash |
| 6.66 | 0.84 | 0.48 | 21.05 | 16.01 | 1.44 | 89.45 | which gives:

| Moles C | Moles per Mole $In_2O_3$ | | | |
|---|---|---|---|---|
| Moles N | $N_2O$ : | $Na_2$ : | $P_2O_5$ : | $Al_2O_3$ |
| 9.2 | 4.78 : | 1.66 : | 54.2 : | 47.3 |

Example J

Indium-containing crystalline silicoaluminophosphate molecular sieve SAPO-5 was synthesized in a manner analogous to EXAMPLE I:

46.2 grams of concentrated phosphoric acid (86.3% $H_3PO_4$) was first diluted with 60.0 grams of de-ionized water then 20.0 grams of Kaiser alumina was added to the solution. This mixture was now digested on a hot plate at 90° C. for 45 minutes, with continuous sitrring. At the end of the digestion period, a solution containing 2.36 grams of indium nitrate dissolved in 82.0 grams of de-ionized water was stirred into the gel. Next 74.0 grams of 40% wt TEAOH solution was sitrred into the gel. This mixture was now stirred at room temperature until a uniform hydrogel was produced. The resulting hydrogel was transferred to a one-liter stainless-steel autoclave. Before sealing the autoclave, 2.04 grams of tetraethylorthosilicate was transferred to the autoclave. The autoclave was then sealed and heating and stirring was begun immediately. The resulting reaction mixture can be described by the following mole ratios:

| | |
|---|---|
| $P_2O_5/Al_2O_3$ | 1.0 |
| $H_2O/Al_2O_3$ | 59 |
| $H^+/Al_2O_3$ | 7.2 |
| $In_2O_3/Al_2O_3$ | 0.02 |
| $SiO_2/Al_2O_3$ | 0.10 |
| $TEA^+/Al_2O_3$ | 1.0 |

The crystallization of the indium-containing SAPO was carried out at 150° C. with stirring (400 rpm).

At the end of 4 days the autoclave was quenched in a water+ice bath to terminate the crystallization. The solid product was filtered, boiled in water, and re-filtered. After drying under a heat lamp, XRD analysis showed that the reflection lines for the product corresponded to silicoaluminophosphate SAPO-5, a Union Carbide designation for this material.

Chemical analysis of the indium-containing SAPO-5 gave:

| Weight Percent | | | | | | | |
|---|---|---|---|---|---|---|---|
| C | N | Na | P | Al | In | Si | Ash |
| 6.32 | 0.60 | 0.48 | 19.88 | 15.71 | 1.45 | 0.66 | 85.00 | which gave

| Moles C | Moles per Mole $In_2O_3$ | | | | |
|---|---|---|---|---|---|
| Moles N | $N_2O$ : | $Na_2O$ : | $P_2O_5$ : | $Al_2O_3$ : | $SiO_2$ |
| 12.3 | 3.39 | 1.65 | 50.8 | 46.1 | 3.7 |

Example K

Platinum incorporation into the indium-containing silicate of ZSM-5 structure was carried out by direct addition of a platinum compound to the zeolite synthesis reaction mixture as follows:

A solution was prepared by dissolving 2.00 grams of indium nitrate and 13.07 grams of NaOH pellets in 710.28 grams of de-ionized water. After the solids dissolved, 26.6 grams of tetrapropylammonium bromide (TPABr) was dissolved in the solution. Finally 1.29 grams of platinum tetraaminenitrate $[Pt(NH_3)_4(NO_3)_2]$ was dissolved in the solution, and the solution was transferred to a one-liter stainless-steel autoclave. Before sealing the autoclave, 66.67 grams of commercial silica gel (SPEX Industries) was poured into the autoclave. The autoclave was then sealed and heating and stirring was begun immediately. The reaction mixture hydrogel can be described by the following mole ratios:

| | |
|---|---|
| $SiO_2/In_2O_3$ | 300 |
| $H_2O/SiO_2$ | 40 |
| $OH^-/SiO$ | 0.30 |
| $Na^+/SiO_2$ | 0.33 |
| $TPA^+/SiO_2$ | 0.10 |
| $SiO_2/Pt$ | 300 |

The crystallization was carried out at 170° C. with stirring (400 rpm).

After 4 days the autoclave was quenched in a water+ice bath to terminate the crystallization. In the usual manner the solid product was filtered, boiled in water, and finally filtered again before drying under a heat lamp. XRD analysis of the solid product showed the material to be crystalline zeolite ZSM-5.

Chemical analysis of the indium-containing ZSM-5 product gave:

| Weight Percent | | | | | | | |
|---|---|---|---|---|---|---|---|
| C | N | Na | In | Pt | $SiO_2$ | $Al_2O_3$ | Ash |
| 8.27 | 0.74 | 1.3 | 1.1 | 0.52 | 82.7 | 0.0265 | 85.05 | which gave:

| Moles C | Moles per Mole $In_2O_3$ | | | | |
|---|---|---|---|---|---|
| Moles N | $N_2O$ : | $Na_2O$ : | $Al_2O_3$ : | $SiO_2$ : | Pt |
| 13.1 | 5.52 | 5.90 | 0.05 | 288 | 0.55 |

Example L

A boron-containing zeolite beta was synthesized and then calcined to remove the organic template, by heating first in $N_2$ 25°–530° at 10/min and held 6 hrs. then in air in $N_2$ 25°–530° at 10/min. and held 6 hours.

25 g of the calined zeolite was ion-exchanged with 750 mg $Pt(NH_3)_4 Cl_2$ in 400 ml $H_2O$ at room temperature overnight. The dried material was then calcined in flowing oxygen (100 cc/min.) 25°–350° at ½°/min. and held 1 hour.

10 g of the calcined Pt-containing zeolite was then treated with 0.9 g $In(NO_3)_3 H_2O$ in 200 ml $H_2O$ at room temperature overnight.

The zeolite was filtered and washed.

The In-containing Pt/zeolite was added to 150 ml $H_2O$ and titrated to pH 9.0 with 0.5 MCsOH (1½ hrs). The material was filtered, washed, and dried. The final product contained 0.76% Pt, 11% Cs, 1.1% In, and 0.08% B.

Example M

The synthesis of a binary oxide zeolite having the structure of ZSM-5 was carried out in the two-phase system as in Ser. No. 878,555 filed June 26, 1986. The aqueous phase of the two-phase system comprised 2.8 g In(NO$_3$)$_3 \times$ H$_2$O dissolved in 35 g water to which was added 63 g TPAOH (40% in H$_2$O). Constituting the organic phase was 77.0 g Si(OCH$_3$)$_4$ dissolved in 35 g of 1-hexanol. The mixture was nucleated at 180° C. for 24 hours and crystallized at 200° C. for 144 hours. The final product was filtered and washed. The X-ray diffraction pattern of the dried material proved it to be well-crystallized ZSM-5.

The sample was ammonium-exchanged (1M NH$_4$Cl, twice, 60° C., 20 ml/g zeolite) and calcined. The chemical composition of the ash of a 1000° C. calcined sample was 79.3 wt. % SiO$_2$ and 1.5 wt. % In$_2$O$_3$. The ash residue also contained a small quantity, i.e. 85 ppm, of aluminum.

Temperature-programmed desorption of ammonia indicated an exchange capacity of 0.09 meq/g for the product of this example. The Si/In ratio from TPAD was 190.5. The sample had an Alpha Value of 1.0.

The particle size of the product from this example was about 0.2 microns. The particles were made of pure single crystals with almost cubic appearance.

Example N

The synthesis of Example M was repeated, except that the mixture contained 3.6 g In(NO$_3$)$_3 \cdot$ H$_2$O in the aqueous phase. The product material was filtered and dried. It had the same characteristic ZSM-5 X-ray lines as the product of Example M. The material was calcined and ammonium-exchanged as described in Example M. The chemical composition of the ash of a 1000° C. calcined sample was 78.2 wt. % SiO$_2$ and 3.1 wt. % In$_2$O$_3$. The ash residue also contained a small quantity, i.e. 180 ppm, of aluminum.

Temperature-programmed desorption of ammonia indicated an exchange capacity of 0.21 meq/g for the product of this example. The Si/In ratio from TPAD was 77.9. The sample had an Alpha Value of 2.5.

The particle size of the product from this example was about 0.2 microns. The particles were made of crystals with almost cubic appearance. There were no impurities present.

Examples N-R

The synthesis of Example M was repeated, except that the mixtures contained varying amounts of In(NO$_3$)$_3 \cdot$ H$_2$O. Five preparations were made, with the following compositions:

| Example | N | O | P | Q | R |
|---|---|---|---|---|---|
| Aqueous Phase(g) | | | | | |
| H$_2$O | 40.0 | 40.0 | 35.0 | 40.0 | 40.0 |
| In(NO$_3$)$_3 \times$ H$_2$O | 0.9 | 7.2 | 1.8 | 1.8 | 3.6 |
| TPAOH, 40% | 63.0 | 63.0 | 63.0 | 63.0 | 63.0 |
| Organic Phase(g) | | | | | |
| 1-Hexanol | 60.0 | 60.0 | 35.0 | 60.0 | 60.0 |
| Si(OCH$_3$)$_4$ | 77.0 | 77.0 | 77.0 | 77.0 | 77.0 |

The product materials were filtered and dried. They had the same characteristic X-ray lines as ZSM-5. The materials were calcined and ammonium-exchanged as in Example M. Their properties were as follows:

| Example | N | O | P | Q | R |
|---|---|---|---|---|---|
| SiO$_2$, wt. % | 84.0 | 77.5 | 80.5 | 76.7 | 82.5 |
| In$_2$O$_3$, wt. % | 0.67 | 5.1 | 1.58 | 1.31 | 2.92 |
| Al, ppm | 105 | 65 | 130 | 85 | 60 |
| Exchange Capacity, meq/g | 0.09 | 0.17 | 0.17 | 0.12 | 0.21 |
| Si/In (from TPAD) | 193 | 99 | 95 | 138 | 77 |
| Alpha Value | 1.5 | 1.6 | 1.0 | 1.0 | n.d. |
| Particle size | 2000A | 1 micr | 2000A | 2000A | 2000A |

What is claimed is:

1. A process for producing an unsaturated analog from a hydrocarbon containing an aliphatic moiety of 2 to 5 carbon atoms, comprising contacting said compound with a catalyst, under dehydrogenation conditions, wherein said catalyst consists of 0.01 to 30 weight percent platinum and a non-acidic crystalline microporous material, said material exhibiting the X-ray diffraction pattern of a zeolite selected from the group consisting of ZSM-11, ZSM-12, ZSM-23, ZSM-48 and ZSM-50, and containing indium, the indium content of said material ranging from 0.01 to 20 weight percent; and thereby producing as a product said analog,
   wherein said dehydrogenation conditions include elevated temperatures ranging from 400° C. to 700° C. and a pressure of 0.1 atmosphere to 500 psig.

2. The process of claim 1, wherein said hydrocarbon is selected from the group consisting of ethane, propane, butane and isobutane.

3. The process of claim 1, wherein said hydrocarbon is an olefin of 2 to 5 carbon atoms.

4. The process of claim 1, wherein the aliphatic moiety is substituted by aryl or alkyl aryl in which the alkyl contains 1 to 4 carbon atoms.

5. The process of claim 1, wherein said non-acidic microporous crystalline material contains aluminum in an amount less than 0.1 weight percent.

* * * * *